(12) United States Patent
Viscomi (10) Patent No.: US 8,002,545 B2
(45) Date of Patent: Aug. 23, 2011

(54) CURE THROUGH LAMINATE VENEER APPLICATOR

(76) Inventor: Brian D. Viscomi, Easton, PA (US)

( * ) Notice: Subject to any disclaimer, the term of this patent is extended or adjusted under 35 U.S.C. 154(b) by 524 days.

(21) Appl. No.: 12/220,749

(22) Filed: Jul. 28, 2008

(65) Prior Publication Data

US 2009/0035720 A1    Feb. 5, 2009

Related U.S. Application Data

(60) Provisional application No. 60/962,567, filed on Jul. 30, 2007.

(51) Int. Cl.
*A61C 3/00* (2006.01)
*A61C 3/04* (2006.01)
*A61C 1/14* (2006.01)
*A61C 5/04* (2006.01)

(52) U.S. Cl. ............. 433/141; 433/29; 433/49; 433/226

(58) Field of Classification Search .......... 433/141–163, 433/29–32, 3–4, 49–50, 226–227; 401/9–10; 362/572, 573, 574, 804; 294/1.1
See application file for complete search history.

(56) References Cited

U.S. PATENT DOCUMENTS

| | | | |
|---|---|---|---|
| 4,834,654 A | | 5/1989 | Naussbaum |
| 4,953,902 A | | 9/1990 | Brown |
| 4,993,949 A | | 2/1991 | Hill |
| 5,040,981 A | | 8/1991 | Oliva |
| 5,256,064 A | * | 10/1993 | Riihimaki et al. ............ 433/141 |
| 2003/0215766 A1 | * | 11/2003 | Fischer et al. .................. 433/29 |
| 2004/0229186 A1 | * | 11/2004 | Slone .............................. 433/29 |
| 2007/0141530 A1 | * | 6/2007 | Graham ........................ 433/163 |

* cited by examiner

*Primary Examiner* — Todd Manahan
*Assistant Examiner* — Yogesh Patel (57) ABSTRACT

An instrument to compressively place and bond a restorative covering to the surface of a tooth including a gripping body (4) with a gently tapered mildly angled neck (6) having an applicator holder (8) with an attached compressible applicator with traversing photo cure apertures (12) to permit the passage of a photo curing light.

7 Claims, 11 Drawing Sheets

CURE THROUGH LAMINATE VENEER APPLICATOR

CROSS REFERENCE TO RELATED APPLICATIONS

THIS APPLICATION CLAIMS THE BENEFIT OF PROVISIONAL PATENT APPLICATION Ser. No. 60/962,567 FILED 2007 JUL. 30, BY THE PRESENT INVENTER

FEDERALLY SPONSORED RESEARCH

Not Applicable

SEQUENCE LISTING OR PROGRAM

Not Applicable

BACKGROUND

1. Field of Invention

This invention applies to the field of Dentistry to allow for the controlled placement and curing of a dental veneer.

2. Prior Art

To enhance the esthetic appearance of a tooth, or restore to its anatomical original form it may be necessary to place tooth-like cover or veneer to its facial or outer surface. After the tooth is prepared, an impression of it is sent to a laboratory which fabricates the veneer and returns it to the clinician for insertion into the patient's mouth. The intended tooth's surface is then prepared to receive the veneer by being etched and primed. Having done this, a bonding agent is applied to the inner surface of the veneer, which is then placed on the tooth and photo-cured to effect the veneer's adhesion to the tooth. The placement process presents with a myriad of challenging steps. This is due to the veneer's innate fragility and size. Typically the clinician will manipulate the veneer for priming and placement with his thumb and index finger. He then places the veneer on to the tooth's surface positioning as best he can (the veneer has been fabricated to fit in an exact position). Wearing the required latex gloves adds more ergonomic difficulties to an already challenging step. Slippage, mal-placement, and over expression of bonding agents, are just some of the untoward complications which can result from this. Once properly oriented on the tooth, the clinician then exposes the veneer to a curing light to bond it to the tooth. Ideally, it is desirable that upon placement of the veneer, adequate compression be applied as to express excess bonding resin from the periphery of the veneer prior to application of polymerizing light. The preferred sequence of curing is from the center of the veneer outward. Present placement systems, because of their structural design, present with an opaque attachment apparatus which prevents the transfer of the light curing medium, with a subsequent lack of cured resin in the critical central portion of the veneer. This area must be addressed after the removal of the placement device.

U.S. Pat. No. 4,834,654 to Naussbaum, J. William, May 30, 1989 presents a dental prosthesis applicator which has a generally opaque head covered by an adhesive strip. This opacity does not allow for light transference and hence leaves the critical central portion of the veneer uncured with the initial light application.

U.S. Pat. No. 4,953,902 to Brown, Martin A., Sep. 4, 1990 presents a veneer placement holder that has an opaque adhesively covered transfer member which precludes the transfer of a polymerizing light in the center of the veneer during the initial application. Furthermore this device relies on a sliding plunger to release the veneer when necessary.

U.S. Pat. No. 4,993,949 to Hill, Sheryl L., Feb. 19, 1991 presents as thin rod which relies on the application of an adhesive globular mass to envelop the veneer in an irregular, unpredictable fashion for the purpose of transfer and placement of the intended object.

U.S. Pat. No. 5,040,981 to Oliva, William E., Aug. 20, 1991 presents as a cylindrical tip attached to an extended rod. The tip is festooned with a plurality of flexible tabs meant to engage the veneer for the placement process. These tabs plus their attachment tip are opaque by nature and therefore interfere with the transfer of a light source and subject the veneering process to potential complications.

U.S. Pat. No. 5,256,064 to Riihimaki, Roy E., Oct. 26, 1993 presents as an applicator with disposable double-sided disposable pads which adhere to the instrument head on one side, and engage the veneer with the other. The instrument head and the double-sided foam pad engage the veneer's central portion, and being opaque in nature serve to prevent light transference to the critical central portion of the veneer.

OBJECTS AND ADVANTAGES

Accordingly, several advantages of the present patent application of Brian D. Viscomi for Cure Through Laminate Veneer Applicator are:
 a. Ergonomically contoured to facilitate approach to tooth
 b. Permits exact placement of veneer on tooth surface.
 c. Allows for compression of veneer onto tooth surface in order to express excess resin.
 d. Allows for simultaneous light curing while maintaining the applicator in position.
 e. Permits light transference into the critical central portion of the veneer to effect resin cure from the center out.
 f. Is disposable.

Further objects and advantages are to provide an applicator which is easy to use and is readily disposable, simple to manufacture. Still further objects and advantages will become apparent from a consideration of the ensuing description and drawings.

SUMMARY

In accordance with the present invention, a cure through veneer applicator comprises a an instrument to compressively place and bond a laminate veneer to the surface of a tooth having a gripping body with thereon a compressible body with at least one traversing aperture to permit the passage of a photo curing light during operative bonding of a laminate veneer to a tooth's surface.

REFERENCE NUMERALS

2. Cure through veneer applicator
4. Gripping handle
6. Neck
8. Applicator holder
10. Compressible applicator
12. Photo cure aperture
14. Photo cure groove
16. Holder curing aperture
18. Metal neck
20. Double neck strut
22. Concave applicator surface
24. Transparent neck
26. Stick on applicator
28. Peel off emulsion
30. Adhesive layer
32. Applicator docking insert
34. Applicator docking extrusion
36. Insert aperture
38. Metal applicator insert
40. Transparent plastic applicator insert
42. Adhesive face emulsion
44. Emulsion peel tab
46. Adhesive gripping face
48. Cylindrical compressible applicator
50. Reflective coating
52. Aperture-less compressible applicator
54. Photo cure channel
56. Transparent compressible termination
58. Transparent neck
60. Multi-use instrument applicator
62. Prepared anterior tooth
64. Laminate
66. Compressive applicator forces
68. Photo Curing Light
70. Polymerizing light

DETAILED DESCRIPTION OF THE INVENTION

Figures 1A, 1B, 1C, 1D:
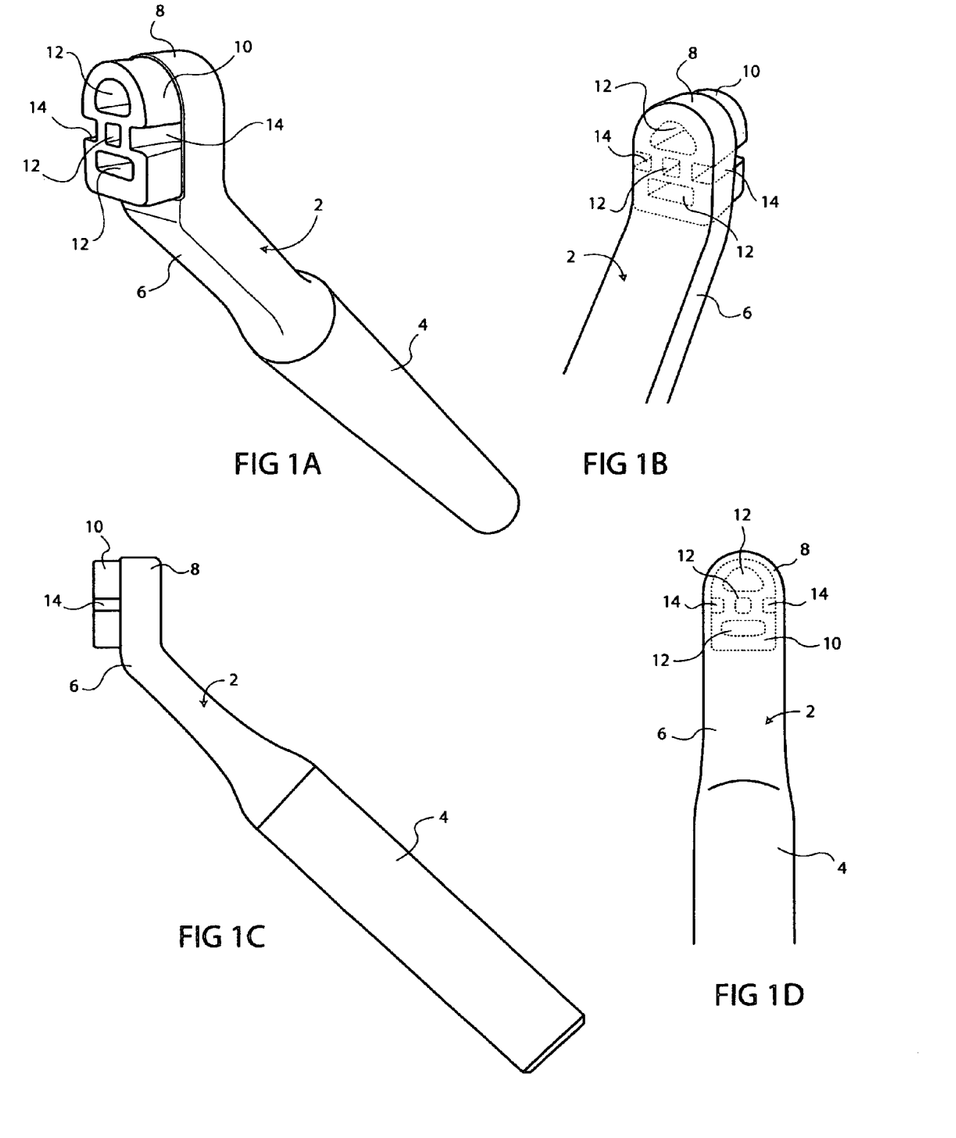
FIGS. 1A to 1D shows various views of a preferred embodiment for the cure through laminate veneer applicator.

FIG. 1A shows a frontal three quarter view of the preferred embodiment. FIG. 1B shows a partial posterior three quarter view of the preferred embodiment. FIG. 1C shows an orthographic lateral view of the preferred embodiment. FIG. 1D shows an orthographic partial posterior view of the preferred embodiment.

The cure through veneer applicator 2 is an elongated body or gripping handle 4 with an applicator holder 8. The handle 4 is desirably similar dimension to currently available instrumentation. The handle's 4 gripping portion extends to a tapered portion or neck 6. The neck 6 has a gentle angle with relation to the handle 4 that desirably accommodates optimal patient/clinician ergonomics and related oral anatomical considerations. Emerging from the neck's 6 tapered terminal regions is a flattened planar expanse or applicator holder 8. The holder 8 is made from a desirably transparent material and has a general tooth shaped dimension. It can, however assume any desirable form as clinical demands merit. The applicator holder 8 is planar structure is designed to attachably accept and hold a compressible termination or compressible applicator 10. The applicator holder 8 can be flat to accept an applicator with an adhesive layer 30 or desirably recessed to accept the applicator with no adhesives 10.

Figure 21:
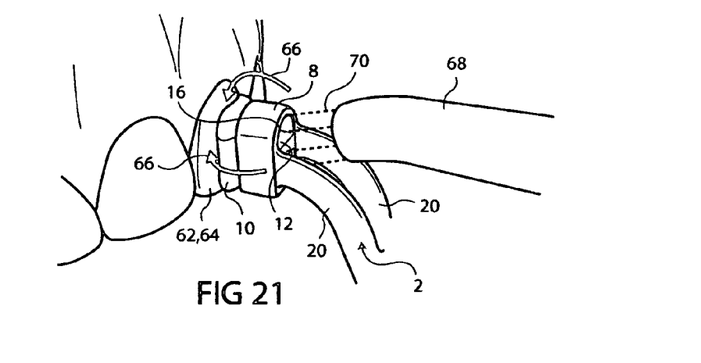
FIG. 21 shows a photo curing light curing a compressively applied veneer to a tooth.

The compressible applicator 10 is a similarly tooth shaped dimension and has a number of traversing holes, perforations or photo cure apertures 12. The apertures 12 extend through the applicators 10 body and are designed to allow direct transmission of a photo curing light source directly to a tooth or a porcelain veneer's surface (FIG. 21). Located on the sides of the compressible applicator 10, integrally formed into the periphery are two laterally opposing grooves or photo grooves 14. The grooves 14 are designed to selectively reduce the compressible applicators 10 area. Selective reduction desirably maximizes the available photo curing footprint to permit maximum light exposure to the surface of a tooth while maintaining broad surface area compressive capabilities.

The cure through laminate veneer applicator 2 can be made and constructed form any number of materials and manufacturing processes. The handle 4 can be made from any desirable metals such as stainless steels or titanium. The handle may be milled, cast, or machined into configuration. The handle may also be made from a synthetic that is injection molded into configuration. Additionally, the applicator 2 can combine both metal and synthetic portion. The handle may be made from metal and have an attached synthetic neck and applicator holder that is comprised of a photon transmissible transparent plastic. The compressible applicator 10 may be made form any suitable compressible material such a foam, silicone, or any other material suitable compressible. The applicator 10 may be injection molded or stamped into configuration.

Alternative Embodiments—FIGS. 2-13

Figure 2A:
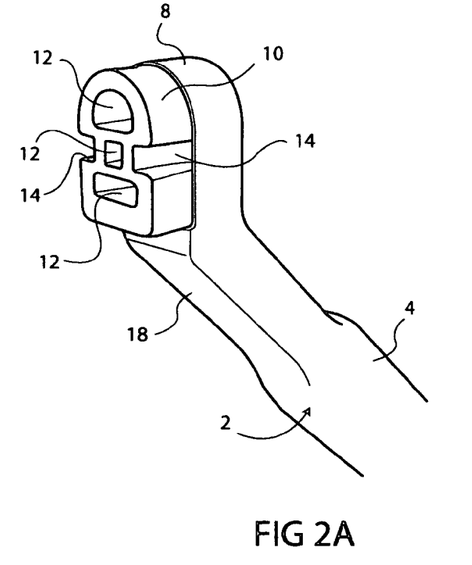
FIGS. 2A to 2C shows various views of a cure through laminate veneer applicator with a cure through aperture formed into the applicator holder's back side.
Figure 2B:
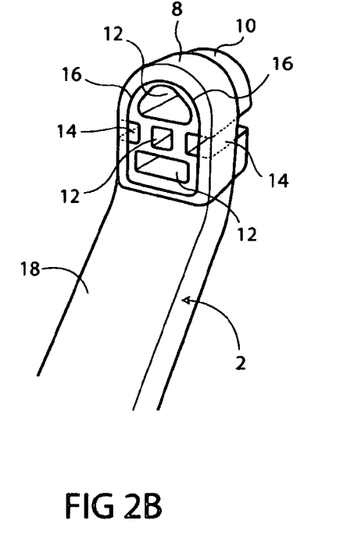
Figure 2C:
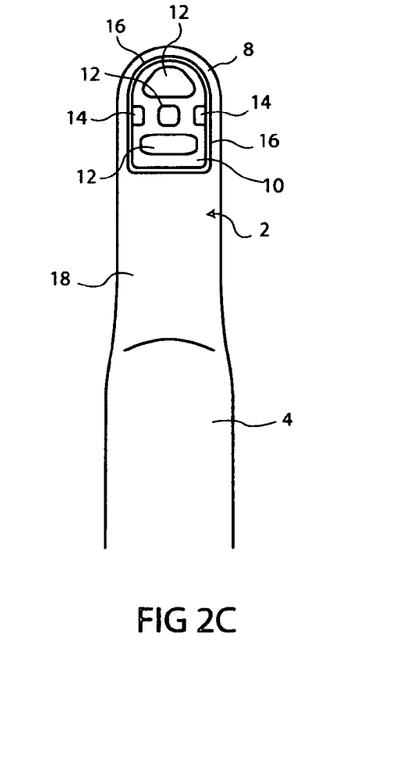
Figure 3A:
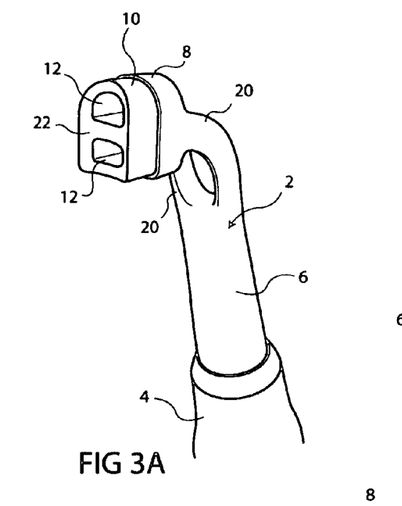
FIGS. 3A to 3D show various views of a cure through laminate veneer applicator with double neck struts and a concave applicator surface.
Figure 3B:
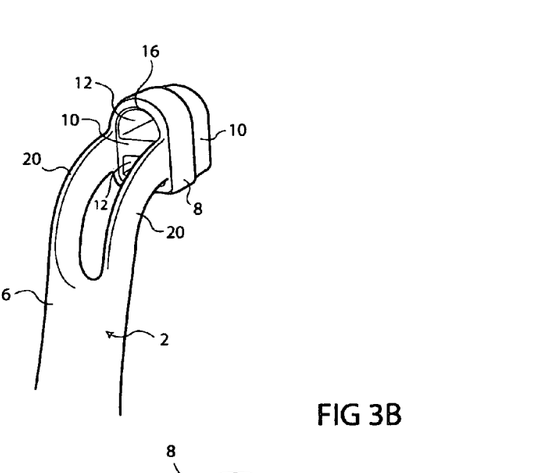
Figure 3C:
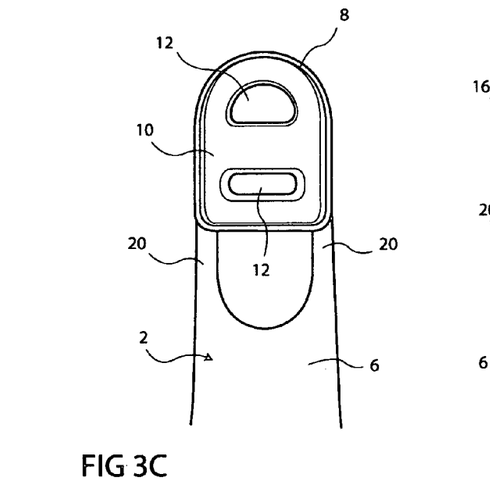
Figure 3D:
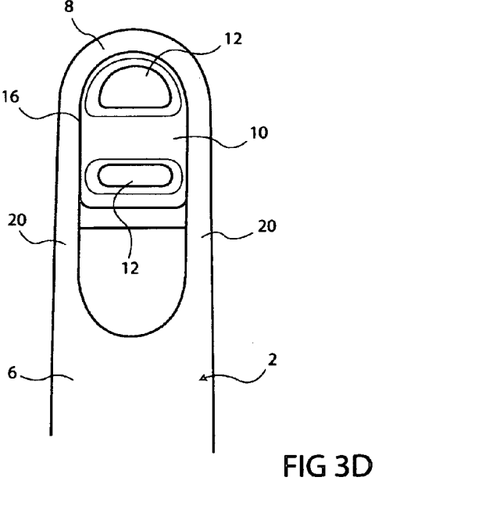
Figure 4A:
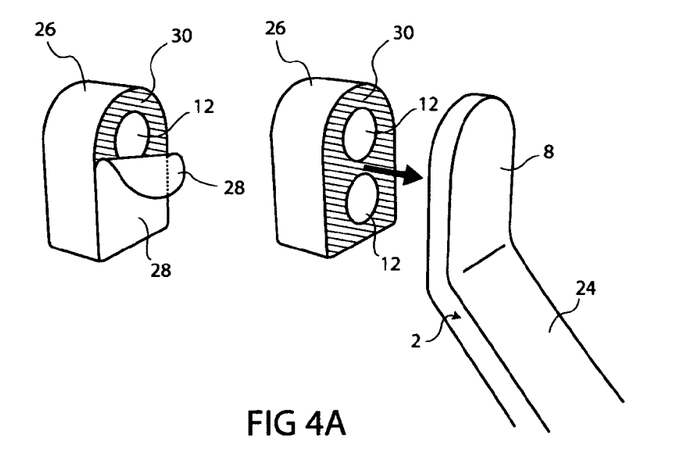
FIGS. 4A to 4C show various views of a veneer applicator with a stick on compressible applicator having a peel off emulsion.
Figure 4B:
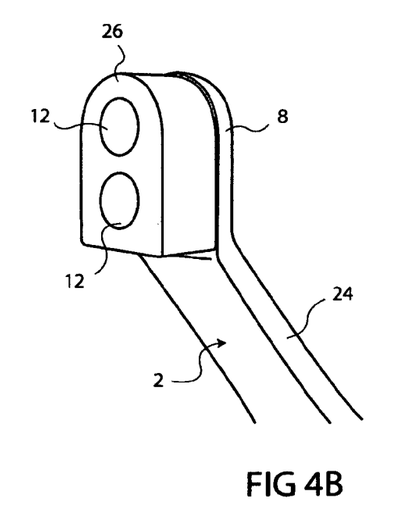
Figure 4C:
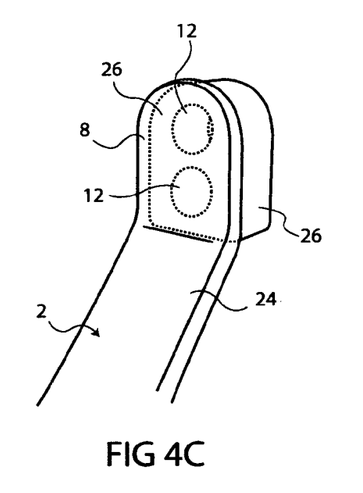
Figures 5A, 5B:
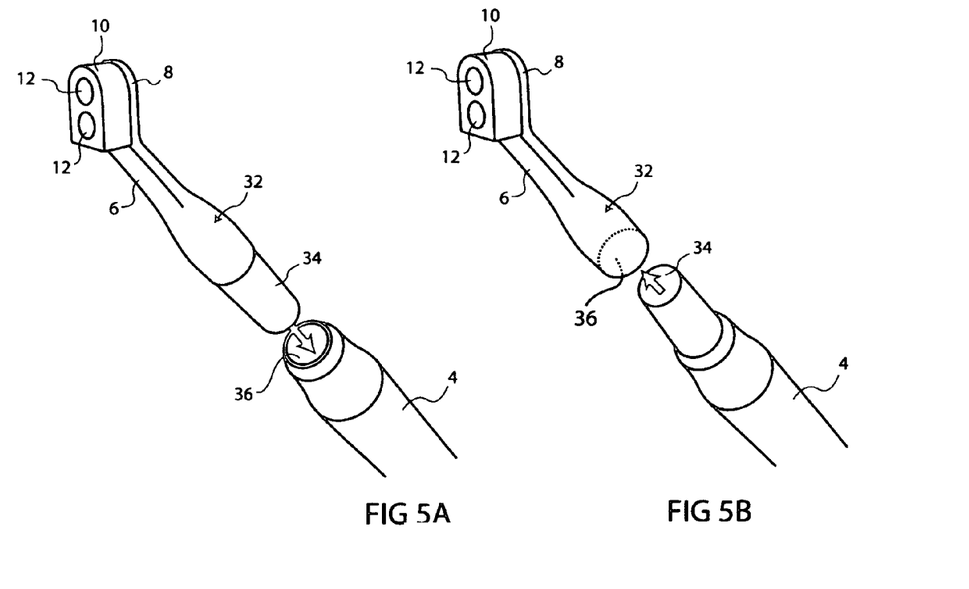
FIGS. 5A to 5B shows a cure through applicator insert docking with a handle.
Figures 6, 7:
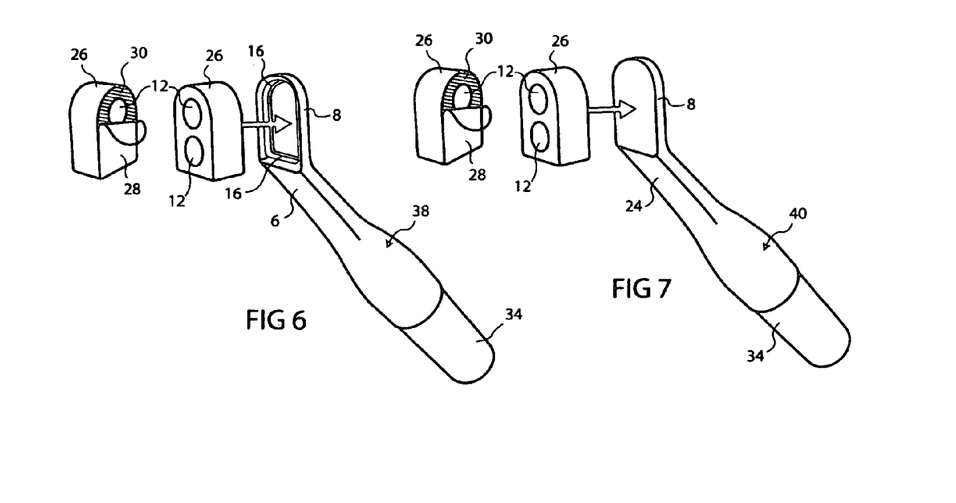
FIG. 6 shows an autoclavable metal cure through applicator insert with a cure through aperture in the applicator's holder.
FIG. 7 shows a disposable transparent cure through applicator insert.
Figures 8A, 8B, 8C:
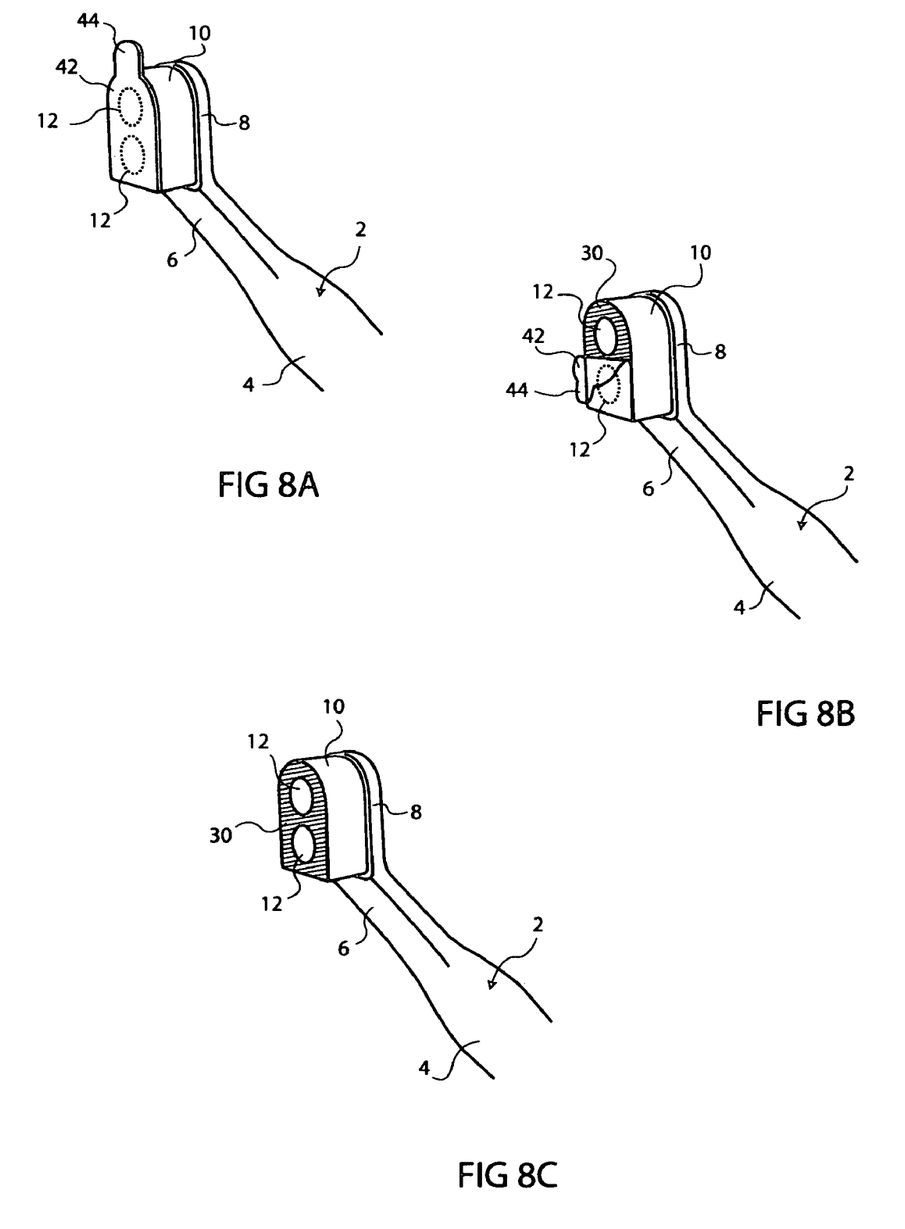
FIGS. 8A to 8C show a cure through laminate veneer applicator with an adhesive gripping face and an attached peel off emulsion.

FIGS. 2A through 2C show an applicator 2 with a metal neck 18 and a holder curing aperture 16 located on the posterior face of the holder 8. FIGS. 3A to 3D show an applicator 2 with a double strut neck 20 and a compressible applicator 10 having a concave applicator surface 22. FIGS. 4A to 4C show an applicator 2 that accepts an independent stick on applicator 26. The stick on applicator 26 has an attached peel away emulsion 28 that exposes and adhesive layer 30 designed to communicate with the cure through applicator's 2 applicator holder 8. FIG. 5A shows an applicator 2 that has an applicator docking insert 32 with a docking extrusion 34 that is designed to interface with a insert docking aperture 36 incorporated into the handle 4. FIG. 5B shows a docking insert 32 with an insert aperture 36 and a handle with a docking extrusion 34. FIG. 6 shows a re-usable metal applicator insert 38 that is has a holder curing aperture 16. FIG. 7 shows a disposable transparent plastic applicator insert 40 with an aperture-less compressible applicator holder 8. FIGS. 8A to 8C shows an applicator 2 with an adhesive gripping face 46 applied to the facial portion. The gripping face 46 has an adhered adhesive face emulsion 42 with an emulsion peel tab 44.

Figures 9A, 9B:
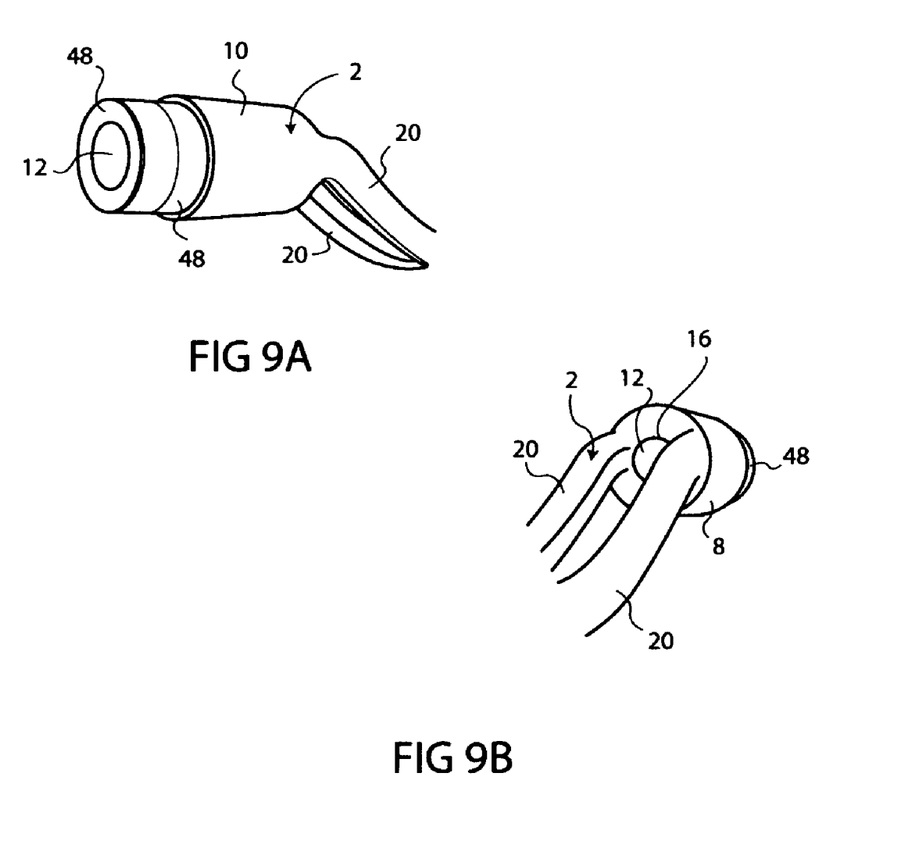
FIGS. 9A to 9C show various views of a cylindrical compressible veneer applicator.
Figure 9C:
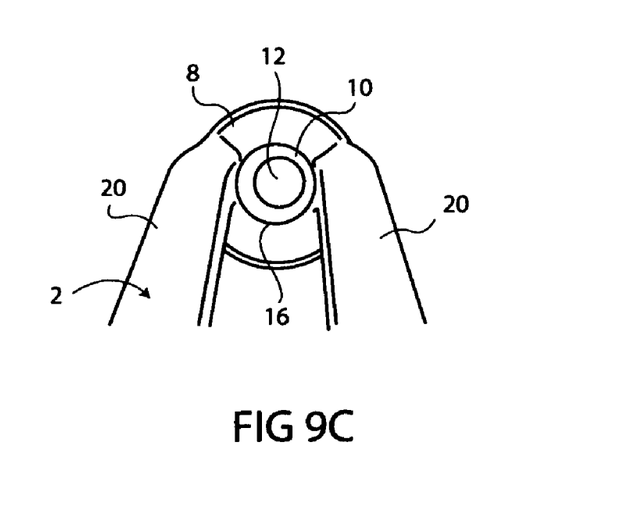
Figure 10:
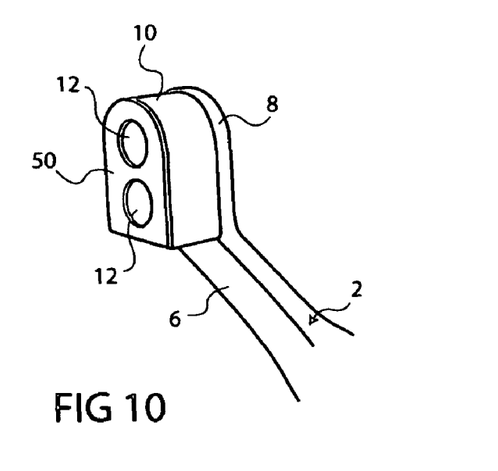
FIG. 10 shows a compressible applicator with a photo reflective coating.
Figure 11:
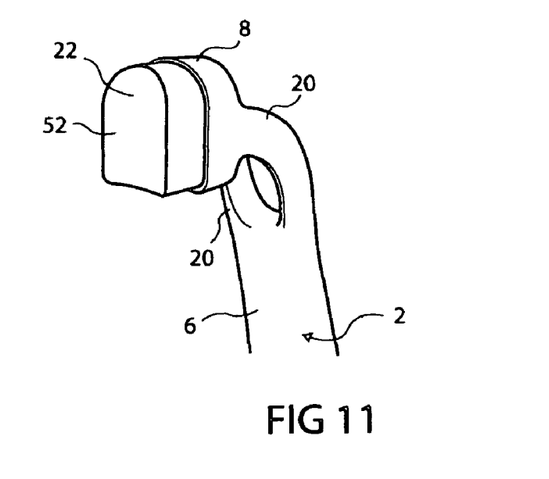
FIG. 11 shows an applicator with an aperture-less compressible applicator.
Figure 12:
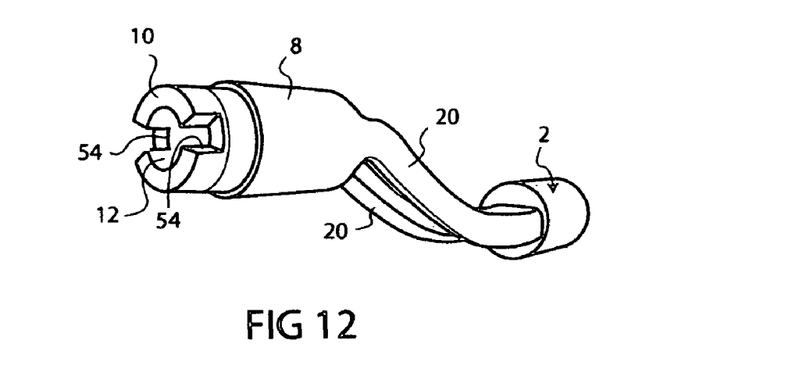
FIG. 12 shows a cylindrical compressible applicator with light channels.
Figure 13:
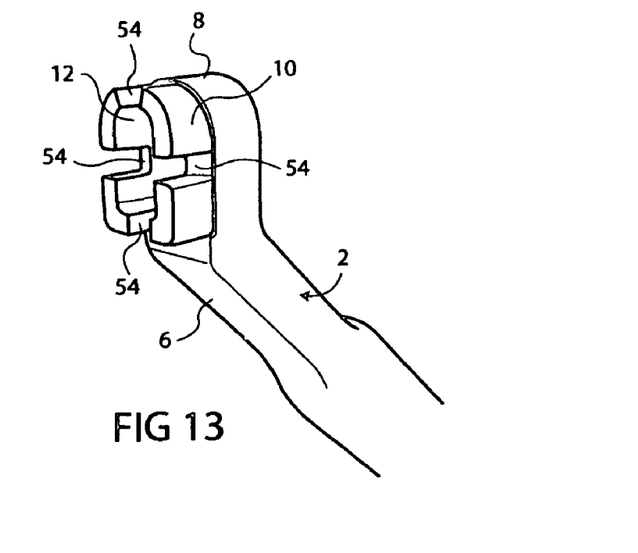
FIG. 13 shows the compressible dental instrument of claim 9 wherein said interlocking insert is comprised of a reusable material having one or more photo transmissible apertures.

FIGS. 9A to 9C show an applicator 2 with a cylindrical compressible applicator 48. FIG. 10 shows an applicator having a reflective coating 50 applied to the compressible applicators 10 facial surfaces. The coating 50 is designed to channel reflected light back onto the curing surfaces. FIG. 11 shows an applicator 2 with an aperture-less applicator 52 having no light curing apertures 12. FIG. 12 shows a cylindrical compressible applicator 48 with photo cure channels 54. FIG. 13 shows an anatomically shaped compressible applicator 10 with photo cure channels 54.

Figure 14:
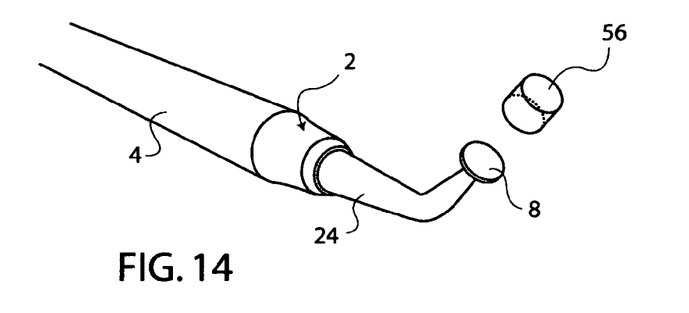
FIG. 14 shows an applicator with a flat flared compressible applicator holder and a photo transmissible rubberized compressible applicator.
Figure 15:
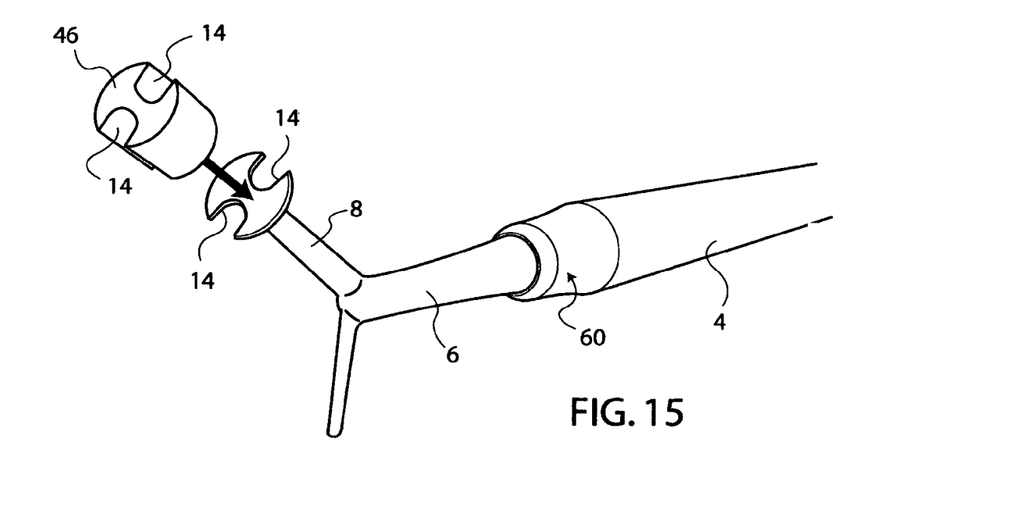
FIG. 15 shows a conventional dental instrument having a flat applicator holder with photo curing grooves to accept a compressible applicator with correlating photo curing grooves.
Figure 16A:
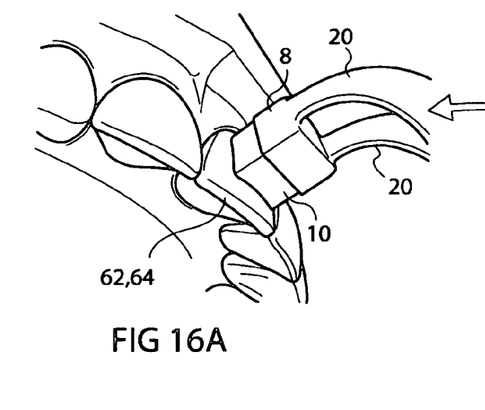
FIGS. 16A to 16B shows an upward looking view of an applicator applying a laminate veneer to a tooth.
Figure 16B:
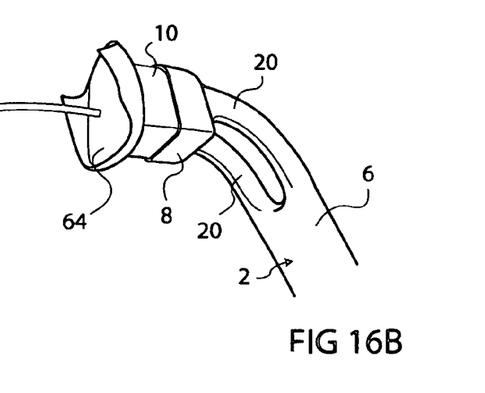

FIG. 14 shows an applicator 2 with a flared planar applicator holder 8 to accept an adhesively applied transparent compressible applicator 56. FIG. 15 shows an applicator 2 with a flared planar applicator holder 8 with photo cure grooves 14 to accept an adhesively applied compressible applicator with photo cure grooves 14

Operation

To use the cure through laminate veneer applicator 2, an operator first obtains a laminate veneer 64 to be applied to the surface of a prepared tooth 62. Next, the operator adheres the veneer 64 to the applicators 2 compressible applicator 10 (not shown). Adhering the veneer 58 to the applicator 10 can be accomplished by independently applying a suitable adhesive substance or by using a pre applied adhesive layer 30 on the compressible applicators facial surface. Once applied, the operator can desirably prepare the veneer 64 for direct application to the tooth 56 surface. Next, gripping the handle 4, the operator guides the adhered veneer 64 to the surface of the prepared tooth 54 (FIGS. 14A, 14B, 15A, 15B, 16).

Figure 17A:
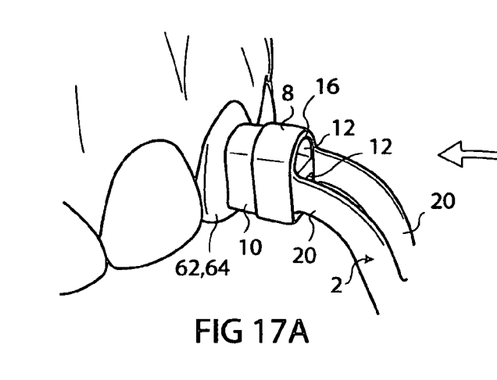
FIGS. 17A to 17B show an eye level view of a laminate veneer being applied to a tooth.
Figure 17B:
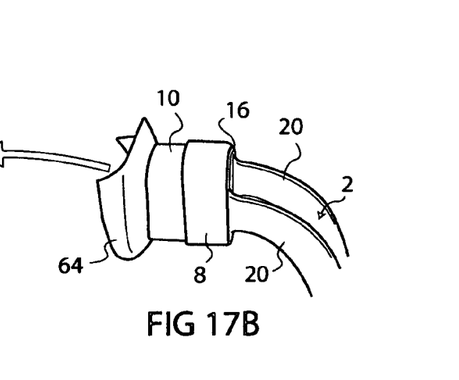
Figure 18:
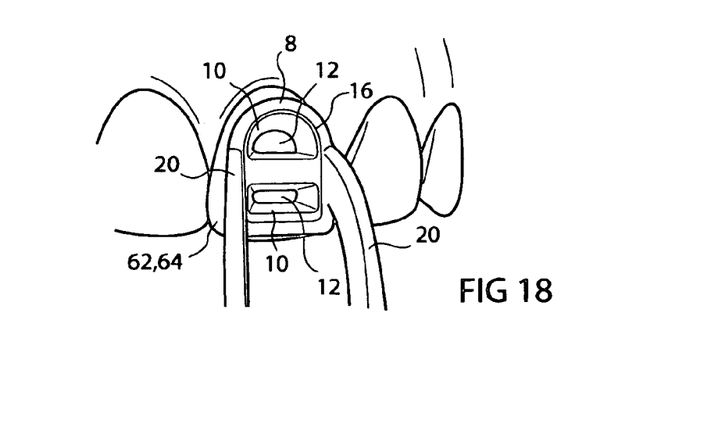
FIG. 18 shows an operative point of view of the applicator, applied veneer and the compressible applicator's cure through apertures.
Figure 19A:
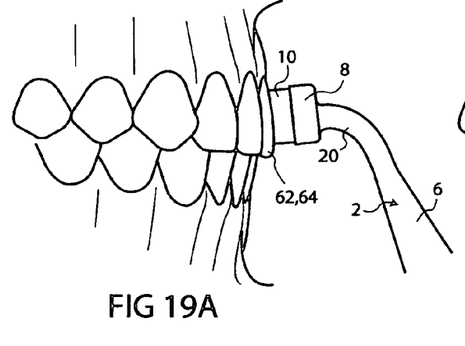
FIGS. 19A to 19B show a lateral view of a veneer applied to a tooth with an uncompressed applicator and an applicator applying compressive forces.
Figure 19B:
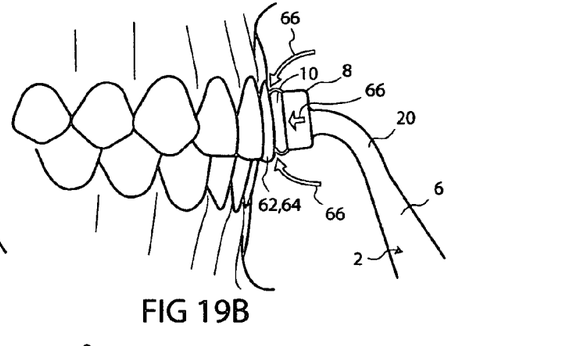
Figure 20:
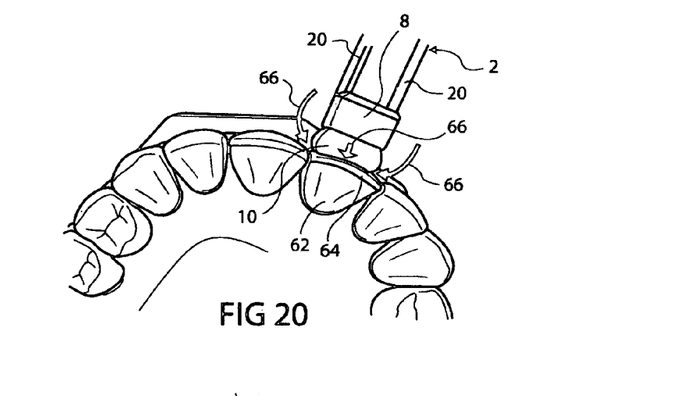
FIG. 20 shows an inferior maxillary view of an applicator compressively applying a veneer.

After desirable alignment, the operator proceeds to correlate and place the veneer 64 on the tooth. Next, applied gentle force compresses the applicator 10 creating compressive forces 66 against the veneer 64 to express uncured bonding substances and create a uniform placement (FIGS. 17A, 17B, 18). During compression (and prior to curing), the operator can proceed to clean up any expressed excess bonding material (not shown). Next, while under compression, a photo curing light 68 is positioned to the posterior aspect of the applicator holder 8 and turned on (FIG. 19). The position of the emitting light source 68 should be in alignment with the cure through apertures 12 and light channels 14. Proper alignment allows the passage of the curing light 70 to directly contact the veneer 64 surface and achieve final bonding.

Conclusion Ramifications and Scope

Accordingly, the reader will see that the cure through laminate veneer applicator can be used to ergonomically prepare, place and bond a porcelain laminate veneer to the surface of a tooth. Compressively applying the veneer with a broad surface provides optimal adhesion, correlation, and expression of bonding agents. Cure through aperture furthermore allow for a pervasive area curing of the veneer to the tooth surface without having to release or diminish the holding compressive forces. The result is a superiorly bonded veneer with maximum ergonomic ease of placement and photo curing. Furthermore, the cure through compressible veneer applicator has additional advantages in that:

The adaptable compressible applicator permits custom tooth veneer conformation regardless of tooth shape Soft compressible surface is gentle to gingival tissue Cure through apertures can have any configuration Can be made in a number of sizes and configurations Although the description above contained much specificity, these should not be construed as limiting the scope of the invention but merely as providing illustrations of some of the presently preferred embodiments of this invention. Namely, the handle portion of the applicator can have any dimension and size that permits optimal grasping. The handle can include recessed apertures to accept any number of docking inserts and necessitated by clinical needs. The neck portion of that applicator can have any size or dimension and may contain a plurality of struts as clinical needs.

The compressible applicator can be of any size or dimension and contain any number of apertures, channels or grooves. It may additionally have any number of specialized attachments, protrusions or extensions. For example, thin semi photo transmissible wings may be incorporated onto the compressible applicator. These wing extensions occlude the inter-proximal areas of a tooth to allow for reduced light exposure which results in partial curing. This partial cure facilitates inter-proximal cleanup. Applicators may be of any shape: They may be oval, asymmetric or even geometric. The compressible applicator may have any number of specialized coatings or substrates. The compressible applicator can also be multilayered or multi cored thus allowing compressible materials of different densities or porosities to be combined.

Additionally, the cure through compressible applicator may be developed as docking parts. The gripping handle may contain any number of docking apertures to accept inserts having any number of docking extrusions. Conversely, the handle may have any number of docking extrusions or extensions to accept compressible inserts with any number of docking apertures or adhesively applied inserts with any number of extensions or apertures. Inserts with docking apertures may further allow them to be attached with a number of pre existing armamentarium. Furthermore, inserts with docking apertures may assume any structural form as to optimally transmit light from a source while affixed to an pre existing instrument. Lastly, the inserts and handle may include any number of mechanisms to facilitate a stable communication. This includes snap in place mechanisms, screw threading, frictional engaging mechanisms, magnets and exteriorly applied adhesive to any surface necessary.

Thus, the scope of the invention should be determined by the appended claims and their legal equivalents, rather than by the examples given.

I claim:

1. A dental instrument to place and bond a laminate veneer to a tooth surface comprising:
   (a) a gripping handle having a longitudinal axis and a transparent applicator holder at a distal end thereof, wherein said applicator holder extends at an angle with respect to the longitudinal axis of said handle; and
   (b) a compressible substantial planar applicator having a front surface and a rear surface, said rear surface removably attached to the applicator holder comprising curved top and a flat bottom and lateral sides extending therebetween so as to correlate with a tooth dimension, wherein said compressible applicator further comprises apertures extending therethrough from the front surface to the rear surface and wherein said lateral sides have photo curing grooves that extend transverse to the front and rear surfaces, to allow direct transmission of a photo-curing light source to allow direct transmission of a photo-curing light source.

2. The dental instrument of claim 1 wherein said applicator holder comprises a recess for receiving said compressible applicator.

3. The dental instrument of claim 1 wherein said compressible applicator comprises an adhesive on said front surface to removably attach to said laminate veneer.

4. The dental instrument of claim 1 wherein said compressible applicator is formed of an open cell foam.

5. The dental instrument of claim 1 wherein said compressible applicator is formed of a closed cell foam.

6. A dental instrument to place and bond a laminate veneer to a tooth surface comprising:
   (a) a gripping handle comprising a docking aperture to attachably receive the docking extrusion of an applicator holder,
   (b) an applicator holder comprising said docking extrusion interfaces with said docking aperture, wherein said applicator holder terminates in a transparent planar surface,
   (c) a compressible substantial planar applicator having a front surface and a rear surface, said rear surface removably attached to the applicator holder, comprising curved top and a flat bottom and lateral sides extending therebetween so as to correlate with a tooth dimension, wherein said compressible applicator further comprises apertures extending therethrough from the front surface to the rear surface and wherein said lateral sides have photo curing grooves that extend transverse to the front and rear surfaces to allow direct transmission of a photo-curing light source, to allow direct transmission of a photo-curing light source.

7. The dental instrument of claim 6 wherein said applicator holder comprises a recess for receiving said compressible insert.

* * * * *